United States Patent
Lang et al.

(10) Patent No.: US 8,431,394 B2
(45) Date of Patent: Apr. 30, 2013

(54) ANTIBODY OR FRAGMENT THEREOF RECOGNIZING AVITAG™ AND USES THEREOF

(75) Inventors: Francois Lang, Nantes (FR); Karine Bernardeau, Coueron (FR); Regis Bouquie, Saint Herblain (FR); Nathalie Labarriere, Nantes (FR)

(73) Assignee: INSERM (Institut National de la Santé et de la Recherche Médicale), Paris (FR)

( * ) Notice: Subject to any disclaimer, the term of this patent is extended or adjusted under 35 U.S.C. 154(b) by 429 days.

(21) Appl. No.: 12/668,119

(22) PCT Filed: Jul. 11, 2008

(86) PCT No.: PCT/EP2008/059125
§ 371 (c)(1),
(2), (4) Date: Jan. 7, 2010

(87) PCT Pub. No.: WO2009/010474
PCT Pub. Date: Jan. 22, 2009

(65) Prior Publication Data
US 2010/0197009 A1      Aug. 5, 2010

(30) Foreign Application Priority Data
Jul. 13, 2007   (EP) .................................... 07301234

(51) Int. Cl.
| | |
|---|---|
| *C07K 16/00* | (2006.01) |
| *C07K 16/44* | (2006.01) |
| *C07K 17/00* | (2006.01) |
| *C07K 17/14* | (2006.01) |
| *C12N 5/16* | (2006.01) |
| *C07K 4/00* | (2006.01) |
| *A61K 39/395* | (2006.01) |
| *A61K 39/44* | (2006.01) |

(52) U.S. Cl.
USPC ...................... 435/326; 530/388.1; 530/391.1

(58) Field of Classification Search .................. None
See application file for complete search history.

(56) References Cited

FOREIGN PATENT DOCUMENTS

| EP | 1437366 | 7/2004 |
|---|---|---|
| WO | 96/05287 | 2/1996 |
| WO | 2006/024875 | 3/2006 |

OTHER PUBLICATIONS

Sears, D.W., Aug. 29, 2009, 2 pages, www at mcdb-webarchive.mcdb.ucsb.edu/sears/immunology/Antibody-Antigen/anti-hel-over.*
GenScript, www at genscript.com/antibody/A01738-AVI_Tag_Antibody_mAb_Mouse.html, 2 pages, Mar. 23, 2012.*
Ansuini et al., Nucleic Acids Res., 30(15):78 (2002).
Robeva et al., J. Int. Soc. Analytical Cytology, 51(2):59-67 (2003).
Guillaume et al., J. Immunol., 177:3903-3912 (2006).
Knabel et al., Nat. Med., 8(6):631-637 (2002).
Hugues et al., J. Immunol. Methods, 268:83-92 (2002).
"Anti C-terminus avitag antibody" [online], Mar. 4, 2007, retrieved from the internet: worldwideweb@.avidity.com/ctermmab.html.
"Biotin AvitagTM Products" [online], Dec. 18, 2005, retrieved from the internet: worldwideweb@.genecopoeia.com/product/avitag/catalog.php#abca.

* cited by examiner

*Primary Examiner* — Gerald R Ewoldt
*Assistant Examiner* — Marianne Dibrino
(74) *Attorney, Agent, or Firm* — McAndrews, Held & Malloy, Ltd.

(57) ABSTRACT

The application relates to antibodies which recognize the AviTag™ peptide of sequence MSGLNDIFEAQKIEWHE (SEQ ID No. 1) and to fragments thereof which recognize SEQ ID No. 1, wherein said antibodies or said fragments thereof recognize polypeptides containing SEQ ID No. 1 at their NH2 terminus and polypeptides containing SEQ ID No. 1 at their COOH terminus. The application further relates to a method for sorting target cells presenting on their surface a surface marker from a mixed cell population comprising the steps of: a) incubating said mixed cell population with a tagged adapter which binds to said surface marker of said target cells, wherein said adapter is bound to an antibody which recognizes said tag, and wherein said antibody is immobilized on a solid support. b) collecting said target cells.

5 Claims, 6 Drawing Sheets

A

Figure 1:
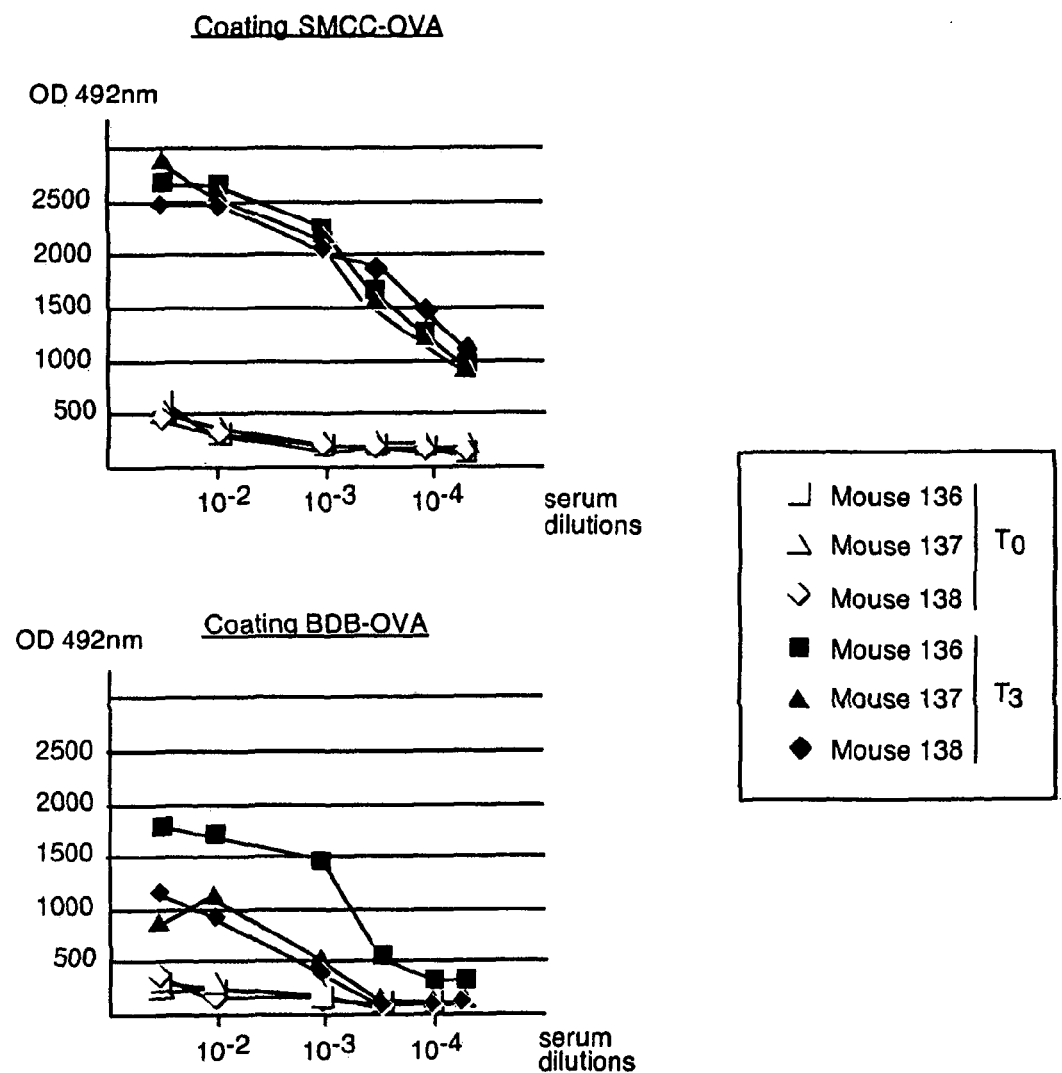

$k_{on}$ (1/Ms) = 1,89 $10^4$
$K_{off}$ (1/s) = 1,94 $10^{-5}$
$K_d$ (M) = 1,03 $10^{-9}$M

B

$k_{on}$ (1/Ms) = 2,32 $10^4$
$K_{off}$ (1/s) = 1,4 $10^{-4}$
$K_d$ (M) = 6,11 $10^{-9}$M

ANTIBODY OR FRAGMENT THEREOF RECOGNIZING AVITAG™ AND USES THEREOF

The present application is filed pursuant to 35 U.S.C. 371 as a U.S. National Phase application of International Patent Application No. PCT/EP08/59125, which was filed Jul. 11, 2008, claiming the benefit of priority to European Patent Application No. 07301234.6, which was filed on Jul. 13, 2007. The entire text of the aforementioned applications is incorporated herein by reference in its entirety.

FIELD OF THE INVENTION

The present invention relates to an antibody or a fragment thereof recognizing a peptide tag and to uses thereof.

BACKGROUND OF THE INVENTION

Use of antibodies specific for peptide tags that have been previously engineered into polypeptides to purify those polypeptides by affinity chromatography and/or to coat those proteins on various solid supports is a widely used strategy and a number of peptide tags and their associated antibodies are already commercially available (GST(glutathion-S-transferase)-tag and GST-specific antibody, Invitrogen; FLAG™-tag and anti-FLAG™ antibodies, Sigma-aldrich Co, Strep-Tag™ and Anti-Strep-Tag™ antibodies, IBA . . . ).

The AviTag™ Technology

The AviTag™ sequence (U.S. Pat. Nos. 5,932,433, 5,874,239 & 5,723,584) is a unique peptide, just 15 residues long, that is recognized by biotin ligase (Schatz P. J., 1993). In the presence of ATP, the ligase specifically attaches biotin to the lysine residue in this sequence. Using vectors, the AviTag™ can be genetically fused to a much bigger polypeptide. This feature effectively allows any polypeptide that has been cloned to be tagged with a biotin molecule.

The originality of the AviTag™ is that this peptide can be biotinylated by the *E. Coli* enzyme BirA. Thus, polypeptides containing this biotinylated peptide either at their NH2 or at their COOH terminus can interact with very strong affinity with streptavidine and can be multimerized or attached to streptavidine-coated surfaces (Altman et al, Science, 1996; Bodinier et al, Nature Medicine, 2000; Rabu et al, J. Biol. Chem., 2005). Moreover, in vivo or in vitro biotinylation of polypeptides is possible.

The use of AviTag™ is growing rapidly in various industrial and medical applications that demand an efficient and robust immobilization technology, including biosensors, diagnostics, proximity assays and drug screening.

Cell Sorting Technology:

One of the possible uses of AviTag™ is its engineering into MHC heavy chains to form tagged MHC/peptide complexes and to further make tetramers of MHC/peptide complexes with streptavidin. These MHC/peptide tetramers specifically bind to T lymphocytes bearing the corresponding T cell receptors (TCR) (Altman et al, Science, 1996, patent WO96/26962) and are now widely used to monitor specific T cell responses in man and in animal models.

Similar biotinylated MHC/peptides complexes coated on streptavidin magnetic beads have been used to design a very efficient sorting procedure to isolate T lymphocytes specific for these complexes (Bodinier et al, Nature Medicine, 2000 and patent WO 0118053). However, biotin-streptavidin interaction is so strong ($Kd=10^{-15}$ M) that it is almost irreversible and so, once bound to streptavidin-coated surfaces polypeptides containing the biotinylated AviTag™ cannot be detached. This has two major consequences:

Biotinylated polypeptides cannot be purified on streptavidine columns because elution is almost impossible;

When biotinylated polypeptides are coated on beads to sort specific cells bearing the corresponding ligands on their surface, the beads may remain bound to the cells for long periods of time and thus trigger transduction events that may have deleterious effects on the selected target cells.

This second point has been well documented in recent publications in the case of the induction of apoptosis of specific T lymphocytes following incubation with MHC/peptides multimers. It was shown that incubation with MHC/peptides complexes of high valence containing short linkers induced rapid apoptosis of T lymphocytes in culture (Cebecauer et al, J. Immunol., 2005). This apoptosis was due to prolonged activation of these T lymphocytes by persistent cross-linking of their TCR.

A number of technical solutions have been proposed to increase the dissociation of MHC/peptide multimers and thus reduce apoptosis of sorted T lymphocytes. This was performed either by engineering a new short tag with reduced affinity for streptavidin into the MHC heavy chain (Strep-Tag™) and sort with magnetic beads coated with a modified streptavidin (Streptamers™, IBA) or by using desthiobiotin instead of biotin to make reversible MHC/peptide tetramers and then sort labelled cells by fluorescence-activated cell-sorting (Guillaume et al, J. Immunol. 2006). Both methods require the addition of an excess of free biotin to compete out the tagged MHC/peptide complexes from streptavidine and thus dissociate MHC/peptide multimers from the sorted cells.

Thus, there is still an important need for a tool which enables to reversibly attach a polypeptide bearing the AviTag™ on a solid support.

SUMMARY OF THE INVENTION

In fulfilling this need, the present invention relates to antibodies which recognize the AviTag™ peptide of sequence MSGLNDIFEAQKIEWHE (SEQ ID No. 1) and to fragments thereof which recognize SEQ ID No. 1, wherein said antibodies or said fragments thereof recognize polypeptides containing SEQ ID No. 1 at their NH2 terminus and polypeptides containing SEQ ID No. 1 at their COOH terminus.

The invention also relates to methods using said antibodies and said fragments thereof, in particular for detection, screening, purification and sorting purposes.

The invention further relates to a method for sorting target cells presenting on their surface a surface marker from a mixed cell population comprising the steps of:

a) incubating said mixed cell population with a tagged adapter which binds to said surface marker of said target cells, wherein said adapter is bound to an antibody which recognizes said tag or a fragment thereof which recognizes said tag, and wherein said antibody or fragment thereof is immobilized on a solid support.

b) collecting said target cells.

DETAILED DESCRIPTION OF THE INVENTION

Antibodies and Fragments Thereof

SEQ ID No. 1 corresponds to the peptide MSGLNDIFEAQKIEWHE, also known in the art under the commercial name AviTag™.

The present invention relates to antibodies which recognize the sequence MSGLNDIFEAQKIEWHE (SEQ ID No. 1) and to fragments thereof which recognize SEQ ID No. 1, wherein said antibodies or said fragments thereof recognize polypeptides containing SEQ ID No. 1 at their NH2 terminus and polypeptides containing SEQ ID No. 1 at their COOH terminus.

Antibodies, also known as immunoglobulins, comprise two heavy chains linked to each other by disulfide bonds and two light chains, each of which is linked to a heavy chain by a disulfide bond. The specificity of an antibody resides in the structural complementarity between the antigen combining site of the antibody (or paratope) and the antigen determinant (or epitope). Antigen combining sites are made up of residues that are primarily from the hypervariable or complementarity determining regions (CDRs). Occasionally, residues from nonhypervariable or framework regions influence the overall domain structure and hence the combining site.

As used herein, the expression "a fragment of antibody" includes any protein or polypeptide-containing molecule that comprises at least a portion of an immunoglobulin molecule such as to permit specific interaction between said molecule and an antigen (e.g. SEQ ID No. 1). The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof. Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Fragments of antibodies according to the invention include, but are not limited to, Fab (e.g., by papain digestion), F(ab')$_2$ (e.g., by pepsin digestion), Fab' (e.g., by pepsin digestion and partial reduction) and Fv or scFv (e.g., by molecular biology techniques) fragments.

Said Fab fragment of the present invention can be obtained by treating an antibody which recognizes SEQ ID No. 1 with the protease papaine. Also, the Fab may be produced by inserting DNA encoding Fab of the antibody into a vector for prokaryotic expression system or for eukaryotic expression system, and introducing the vector into a procaryote or eucaryote to express the Fab.

Said F(ab')$_2$ of the present invention may be obtained by treating an antibody which recognizes SEQ ID No. 1 with the protease pepsin. Also, the F(ab')$_2$ can be produced by binding Fab' described below via a thioether bond or a disulfide bond.

Said Fab may be obtained by treating F(ab')$_2$ which specifically recognizes SEQ ID No. 1 with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote for its expression.

Said Fv fragment may be produced by restricted cleavage by pepsin at 4° C. and pH 4.0. (a method called "cold pepsin digestion"). The Fv fragment consists of the heavy chain variable domain ($V_H$) and the light chain variable domain ($V_L$) held together by strong noncovalent interaction.

Said scFv fragment may be produced by obtaining cDNA encoding the $V_H$ and $V_L$ domains as previously described, constructing DNA encoding scFv, inserting the DNA into an expression vector for prokaryote or an expression vector for eukaryote, and then introducing the expression vector into a prokaryote or eukaryote to express the scFv.

Antibodies according to the invention may be derived from a number of species including, but not limited to, rodent (mouse, rat, rabbit, guinea pig, hamster, and the like), porcine, bovine, equine or primate and the like.

Procedures for raising "polyclonal antibodies" are well known in the art. For example, polyclonal antibodies can be obtained from serum of an animal immunized against SEQ ID No. 1, which may be produced by genetic engineering for example or by peptide synthesis according to standard methods well-known by one skilled in the art. Typically, such antibodies can be raised by administering SEQ ID No. 1 subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times at six weeks' interval. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al., 1988.

Antibodies or fragments thereof according to the invention are further selected for their ability to recognize polypeptides containing SEQ ID No. 1 at their NH2 terminus and polypeptides containing SEQ ID No. 1 at their COOH terminus. Methods for selecting antibodies or fragments thereof according to the invention comprise the use of any method for determining whether a particular antibody or fragment thereof binds to a particular ligand (such as Western blotting, ELISA methods etc.) using as ligands both polypeptides containing SEQ ID No. 1 at their NH2 terminus and polypeptides containing SEQ ID No. 1 at their COOH terminus.

In a preferred embodiment the antibody of fragment thereof according to the invention is a monoclonal antibody or fragment thereof.

As used herein the expression "monoclonal antibody" refers to a population of antibody molecules that contains only one species of antibody combining site capable of immunoreacting with a particular epitope.

Laboratory methods for preparing monoclonal antibodies are well known in the art (see, for example, Harlow et al., 1988). Monoclonal antibodies may be prepared by immunizing a mammal such as mouse, rat, primate and the like, with SEQ ID No. 1. The antibody-producing cells from the immunized mammal are isolated and fused with myeloma or heteromyeloma cells to produce hybrid cells (hybridoma). The hybridoma producing the monoclonal antibodies are utilized as a source of the desired monoclonal antibody. This standard method of hybridoma culture is described in (Kohler and Milstein, 1975).

Alternatively, the immunoglobulin genes may be isolated and used to prepare a library for screening for specifically reactive antibodies. Many such techniques including recombinant phage and other expression libraries are known to one skilled in the art.

In a preferred embodiment the antibody or fragment thereof according to the invention is a monoclonal antibody of fragment thereof obtainable by the hybridoma deposited on May 24, 2007 at the COLLECTION NATIONALE DE CULTURES DE MICROORGANISMES (CNCM) in accordance with the terms of the Budapest Treaty under the number CNCM I-3767. *Collection Nationale De Cultures De Microorganismes (CNCM)*, Institut Pasteur, 28 rue du Dr Roux, 75724 Paris Cédex 15, France.

As used herein the term "hybridoma" denotes a cell, which is obtained by subjecting a B cell, prepared by immunizing a non-human mammal with an antigen, to cell fusion with a myeloma cell derived from a mouse or the like which produces a desired monoclonal antibody having an antigen specificity.

In another embodiment, the invention relates to antibodies displaying the same antigen combining sites as the antibody obtainable by the hybridoma deposited at the CNCM under the number CNCM I-3767.

Such antibodies or fragments can be obtained, for example, by methods used for generating humanized ScFv fragments. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

While monoclonal antibodies can be produced by hybridoma culture the invention is not to be so limited. Also contemplated is the use of monoclonal antibodies produced by cloning and transferring the nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; European Patent Publications No. 0239400 to Winter et al. and No. 0125023 to Cabilly et al.

In a further embodiment, the invention further relates to a hybridoma suitable for obtaining monoclonal antibodies which according to the invention.

In a preferred embodiment, the invention relates to the hybridoma deposited at the COLLECTION NATIONALE DE CULTURES DE MICROORGANISMES (CNCM) under the number CNCM I-3767.

A further object of the invention relates to a solid support whereupon an antibody or a fragment thereof according to the invention is immobilized.

Solid supports suitable for immobilizing an antibody of conservative fragment or derivatives thereof according to the invention are well known in the art. They include activated beads and resins such as Agarose or Sepharose, magnetic beads and the like.

In a preferred embodiment, the invention relates to a magnetic bead whereupon an antibody or a fragment thereof according to the invention is immobilized.

An example of magnetic beads suitable for the invention is the M450 epoxy Dynabeads®, which are commercially available from Invitrogen, France, under the reference 140-11.

In another embodiment, the invention relates to an affinity column which contains a solid support whereupon an antibody or a fragment thereof according to the invention is immobilized.

Affinity columns are well known in the art. They comprise a column which contains an immobilized antibody. Said antibody can be immobilized, for example, onto activated agarose beads or sepharose beads, which are commercially available from a variety of manufacturers.

Methods

The invention further relates to any method using an antibody or a fragment thereof according to the invention, in particular for detection, screening, purification and sorting purposes.

A further object of the invention relates to a method for detecting a polypeptide comprising the step of incubating said polypeptide with an antibody or fragment thereof according to the invention, wherein said polypeptide contains SEQ ID No. 1 at its NH2 terminus or COOH terminus.

Such methods for detecting a polypeptide using an antibody which recognizes a tag within said polypeptide are well known in the art. They include, but are not limited to, immunoblotting, radioimmunoassay, ELISA or immunofluorescence techniques.

In such techniques, the antibody or fragment thereof may be labelled with a detectable molecule or substance, such as a fluorescent molecule, a radioactive molecule, or any other labels known in the art (in the so-called primary detection techniques). Labels are known in the art that generally provide (either directly or indirectly) a signal. Alternatively, the antibody or fragment thereof according to the invention can be recognized by another molecule, said other molecule being labelled (in the so-called secondary detection techniques).

In a preferred embodiment the invention relates to a method for screening for a ligand of a polypeptide comprising the step of incubating said polypeptide with an antibody or fragment thereof according to the invention and with a putative ligand, wherein said polypeptide contains SEQ ID No. 1 at its NH2 terminus or COOH terminus.

For example, putative ligands of a polypeptide can be coated in the wells of a microtiter plate and incubated with said polypeptide. The antibody or fragment thereof according to the invention is then added to the wells. In the case of an interaction between said putative ligand and said polypeptide, the antibody will be bound to the well and can be revealed by any primary or secondary technique known in the art.

A further object of the invention relates to a method for purifying a polypeptide comprising the step of incubating said polypeptide with a solid support whereupon an antibody or fragment thereof according to the invention has been immobilized, wherein said polypeptide contains SEQ ID No. 1 at its NH2 terminus or COOH terminus.

Methods for purifying polypeptides using an antibody that recognizes an epitope or a tag are well known in the art. One such method is immunoprecipitation, which comprises in incubating said polypeptide with an immobilized antibody or fragment thereof which recognizes said epitope or tag, and separating the material which is bound to said antibody from the unbound material.

In a preferred embodiment, the method of the invention is the purification of a polypeptide using an affinity column which contains a solid support on which an antibody or fragment thereof according to the invention has been immobilized, wherein said polypeptide contains SEQ ID No. 1 at its NH2 terminus or COOH terminus.

Affinity columns are well known in the art. They can for example be prepared, according to the manufacturers's instructions, by using affinity chromatography reagents and kits commercialised by Biorad, Pierce, GE Healthcare etc.

A further object of the invention relates to a method for sorting cells comprising the step of incubating said cells with a solid support whereupon an antibody or a fragment thereof according to the invention is immobilized, wherein said cells present on their surface a polypeptide containing SEQ ID No. 1 at its NH2 terminus or a polypeptide containing SEQ ID No. 1 at its COOH terminus.

Cell sorting is a commonly used method used in cell biology. Various techniques can be used, such as, Fluorescence Activated Cell Sorting (FACS). Typically, cells are incubated with a fluorescently labelled antibody which recognizes a polypeptide present on the surface on the target cells population. The cells are then forced into a small nozzle of a cell sorter one at a time. They are then scanned by a fluorescence laser, separated according to their fluorescence and the target population can be collected.

In a preferred embodiment, the invention relates to a method for sorting cells comprising the step of incubating said cells with magnetic beads whereupon an antibody or a fragment thereof according to the invention is immobilized, wherein said cells present on their surface a polypeptide containing SEQ ID No. 1 at its NH2 terminus or a polypeptide containing SEQ ID No. 1 at its COOH terminus.

Cell sorting using magnetic beads whereupon an antibody or fragment thereof is immobilized is a currently used technique known as immuno-magnetic isolation.

According to this technique, antibodies are covalently bound to magnetics beads. Cells are incubated with said magnetics beads. Those presenting the polypeptide on their surface will bind to the antibody on the magnetic beads and can be recovered by submitting said beads to a magnetic field. This procedure can be carried out using reagents provided by different manufacturers such as Dynal® or Miltenyi®.

In another embodiment, the invention relates to a method for sorting target cells presenting on their surface a surface marker from a mixed cell population comprising the steps of:
  a) incubating said mixed cell population with a tagged adapter which binds to said surface marker of said target cells,
    wherein said tagged adapter is bound to an antibody which recognizes said tag or a fragment thereof which recognizes said tag, and
    wherein said antibody or fragment thereof is immobilized on a solid support.
  b) collecting said target cells.

According to this embodiment, the immobilized antibody does not directly recognize a tagged polypeptide present on the cell surface of the target cells. Rather, it recognizes a tagged adapter which in turn recognizes a surface marker present on the surface of the target cells. The procedure is carried out in a similar manner to the standard cell sorting techniques.

In a preferred embodiment, said solid support is a magnetic bead.

The term "tagged adapter" as used herein refers to a molecule or stable complex which contains a tag on the one hand and a recognition site for a surface marker on the other hand. By "stable complex" is meant a molecular complex which does not dissociate in the physico-chemical conditions according to the method of the invention.

In a preferred embodiment, a tagged adapter according to the invention is tagged at its NH2 terminus or at its COOH terminus with SEQ ID No. 1 and said antibody is the antibody according to the invention.

The expression "target cells" as used herein refers to the cell population which one wishes to isolate according to the method of the invention.

Typically, any cell presenting a number between 2,000 and 10,000 of a surface marker per cell at its surface can be sorted by the method according to the invention. Examples are cells of the immune system, non-immune blood cells, stem cells, etc.

T lymphocytes are white blood cells which can be involved in the field of anti-viral, anti-bacterial or anti-tumoral immunity and express specific receptors at their surface against CMH-peptide complexes.

In a preferred embodiment, said target cells are T lymphocytes.

The term "surface marker" refers to a molecule or molecular complex which is present specifically at the surface of target cells.

Typically, a surface marker according to the invention is any cell surface receptor specific for a target cell population and for which between 2,000 and 10,000 copies per cell are present.

In a preferred embodiment, said surface marker is a T cell receptor (TCR).

In a preferred embodiment, the tagged adapter is a MHC-peptide complex tagged with SEQ ID No. 1. Each type of TCR binds to a specific peptide presented in the context of MHC-peptide complex. The choice of the specific peptide presented by the MHC is made according to the type TCR present on the surface of the target T lymphocyte.

MHC-peptide complexes tagged with SEQ ID No. 1 are described for example in Vignard et al., 2005.

A particular advantage of the method according to the invention is that each reagent of the method (magnetic beads, antibody and tagged adapter) can be produced in GMP conditions. Therefore, the whole sorting procedure can for example be easily applied to a clinical setting to obtain clinical grade specific T lymphocytes to be use in adoptive cell transfer (ACT) protocols in the fields of cancer and infectious diseases.

This procedure can thus be used to sort clinical grade T lymphocytes directed against any viral, bacterial or tumoral epitopes. These selected T lymphocytes can then be amplified in vitro in GMP conditions as previously described (Vignard et al, J. Immunol., 2005) and used in adoptive immunotherapy protocols.

The invention will be further illustrated through the following examples, figures and tables.

FIGURES

FIG. 1

ELISA screening of sera from three mice against AviTag coupled to ovalbumin (OVA) through its NH2 terminal cystein residue (SMOG-OVA) (top panel) or through its COOH terminal tyrosine (BOB-OVA) (lower panel) before immunization (white symbols, T0) or after the third immunization (dark symbols, T3).

FIG. 2

Dynamic analyses by surface plasmon resonance (BIAcore) of the binding of AvT-6A8 monoclonal antibody immobilized on a CM5 chip to either a recombinant soluble form of 4-1BBL bearing the AviTag at its NH2 terminus (panel A) or to an HLA-A0201/β2 microglobulin/Melan-A peptide complex bearing the AviTag at the COOH terminus of the HLA heavy chain (panel B). Fitting of the curves were performed using a Langmuir model. The calculated kinetic constants indicated that AvT 6A8 has a good affinity for AviTag placed either at the NH2 or at the COOH extremity of a polypeptide with a slight preference for the former.

FIG. 3

Purification of a recombinant complex bearing the AviTag by affinity chromatography with immobilized AvT-6A8. The supernatant of transfected S2 *drosophila* cells producing a soluble DPA0103/DPB0401 class II HLA complex was run onto a HiTrap Column coated with AvT-6A8. The elution profile is shown on panel A. The two peaks were then analyzed by SDS-PAGE followed by silver stain (panel B). Staining revealed only bands of interest (i.e. the full DP complex and the denatured α and β chains) demonstrating the efficiency of the purification procedure.

FIG. 4

Preparation of AvT-6A8 coated beads for T cell sorting. Panel A shows the staining of M450 epoxy beads with a PE conjugated goat anti-mouse (GAM) antibody before (grey histogram) and after (dark histogram) covalent coupling of AvT-6A8. Mean fluorescence intensity (MFI) is indicated on each peak. These AvT-6A8 beads were then incubated (dark histogram) or not (grey histogram) with saturating amounts of an HLA-A2-AviTag/MelanApeptide/β2 microglobulin complex and stained with an FITC-conjugated anti-HLA-ABC antibody (panel B). This analysis demonstrated that a significant amount of HLA-A2-AviTag/MelanApeptide/β2 microglobulin complex was bound to the beads. On panel C is shown the binding of a biotinylated HLA-A2-AviTag/MelanApeptide/β2 microglobulin complex onto streptavidin-coated M280 beads. Staining with anti-HLA-ABC revealed that saturated M280 beads displayed a high amount of HLA2/peptide complexes (MFI 305, white histogram) and thus concentration of biotinylated HLA-A2/peptide was lowered to obtain a staining (MFI 24.5, black histogram) comparable to that obtained with saturated AvT-6A8 coated beads (MFI 31, panel B).

FIG. 5

Immunomagnetic sorting of specific T lymphocytes with AvT-6A8 M450 beads saturated with soluble HLA-A2-AviTag/MelanApeptide/f32 microglobulin complexes. On panel A is shown a double staining with an anti-CD8 antibody and a HLA-A2/melan-A tetramer of a tumor infiltrating T lymphocyte population before the sort (left panel) revealing 6.8% T lymphocytes specific for melan-A/A2 complexes. After one sort with A2/melanA coated AvT-6A8 M450 beads and a 13 day polyclonal expansion in vitro, double staining revealed a population almost pure (97%) in specific T cells (right panel). An identical sort was performed with peripheral blood mononuclear cells (panel B) containing initially 2.2% melan-A specific lymphocytes (left panel) leading to a 95% pure population in specific T lymphocytes after in vitro expansion (right panel).

FIG. 6

Apoptosis induction of two melan-A specific T cell clones by incubation with A2/melanA coated AvT-6A8 M450 beads or with biotinylated A2/melanA coated streptavidin M280 beads. Clone 24B7 and 10C10 were incubated at 37° C. for 5 h or 22 h with AvT-6A8 M450 beads alone or with AvT-6A8 M450 beads saturated with A2/melan-A complexes or with M280 streptavidin beads coated with comparable amounts of A2/melan-A as described above in FIG. 4. The percentage of apoptotic cells was determined by FITC-annexin V and propidium iodide (PI) staining and analysis by flow cytometry. As shown on the two top panels, M280 beads coated with A2/melan-A induced massive apoptosis of both clones after a 5 h incubation with a majority of dying cells stained with annexin V but not PI (early apoptosis). In marked contrast, AvT-6A8 M450 beads saturated with A2/melan-A complexes induced very little apoptosis when compared to M450 beads alone. This was confirmed after a 22 h incubation of clone 24B7 (lower left panel) with the different reagents. An increase in apoptosis was seen with A2/melan-A M280 beads with a majority of the cells now stained with both annexin V and PI (late apoptosis) but not with AvT-6A8 M450 beads saturated with A2/melan-A complexes. For clone 10C10, dying cells could not be detected anymore after a 22 h incubation, probably because they had already turned into debris due to faster apoptosis kinetics (lower right panel).

EXAMPLES

Example 1

Production and Characterization of the AvT-6A8 Monoclonal Antibody

Choice of the Antigens for Immunization and Screening

The aim was to select an antibody that recognizes the peptide MSGLNDIFEAQKIEWHE (SEQ ID No. 1), named AviTag™, when this peptide is encoded in a polypeptide either at the NH2 terminus or at the COOH terminus. To this end, we added a cystein residue at the NH2 end of the AviTag peptide and a tyrosine at the COOH end to be able to chemically couple this peptide to different carrier proteins. Thus, the elongated peptide CMSGLNDIFEAQKIEWHEY (SEQ ID No. 2) was coupled to KLH (Keyhole Limpet Hemocyanin) with the MBS (Maleimido benzoyl N-hydroxy succinidyl ester) agent that makes covalent bound between the cystein of the peptide and lysin residues on KLH. This Avitag-KLH was used to immunize mice. To screen hybridoma supernatants, we coupled the AviTag to a different carrier protein, ovalbumine (OVA) either through its cystein residue with the SMCC (Succinimidyl 4-[N-maleimidomethyl]cyclohexane-1-carboxylate) (named tag-SMCC-OVA) or through its tyrosine residue with BDB (bis diazobenzidine) (named tag-BDB-OVA).

Immunization Protocol

Three BALB/c mice were immunized by 4 IP injections of 50 μg of KLH-AviTag at J0, J30, J60 and J100 with the addition of complete Freund adjuvant for the first injection and incomplete Freund adjuvant for the next injections. Sera from the three mice were tested for their reactivity towards tag-SMCC-OVA and tag-BDB-OVA before immunization and after the third immunization. All mice showed reactivity of their sera against the two antigens although mouse 136 showed a stronger response than the two other mice towards tag-BDB-OVA (FIG. 1). This mouse was selected to realize the fusion.

Fusion, Screening and Cloning of Hybridomas

Splenocytes from mouse 136 ($11.10^7$ cells) were fused with murine myeloma cells SP2/0-AG-14 and seeded at $10^5$ cells/well in 96 well plates in HAT selecting medium. After 15 days in culture, a first screening was performed by ELISA against tag-SMCC-OVA and tag-BDB-OVA. Among the 1075 wells tested, 113 hybridomas were positive. These positive hybridomas were re-tested a week later against tag-SMCC-OVA, tag-BDB-OVA, OVA alone and a recombinant protein comprising the AviTag at its NH2 end, named AviTag-4-1BBL (Rabu et al., J. Biol. Chem., 2005). Eleven hybridomas whose reactivities are shown on Table IA were selected, amplified and frozen. The hybridoma 6A8 was finally chosen because of its highest reactivity towards the peptide AviTag coupled at the NH2 terminus (tag-SMCC-OVA) and COOH terminus (tag-BDB-OVA) of ovalbumine, its strong reactivity towards AviTag-4-1 BBL and its absence of recognition of OVA alone. This hybridoma was cloned and a sub-clone 6A8F4 was selected using the same procedure. This sub-clone was cloned again by limiting dilution to ensure its monoclonality. The reactivity of the two subclones used for production of the antibody is indicated in Table IB. The final monoclonal antibody was named AvT-6A8.

Characterization of the Monoclonal Antibody AvT-6A8

The isotype of the heavy chain of AvT-6A8 is IgG1 as determined by ELISA and the isotype of the light chain is kappa as determined by Isostrip (Roche).

Figure 2:
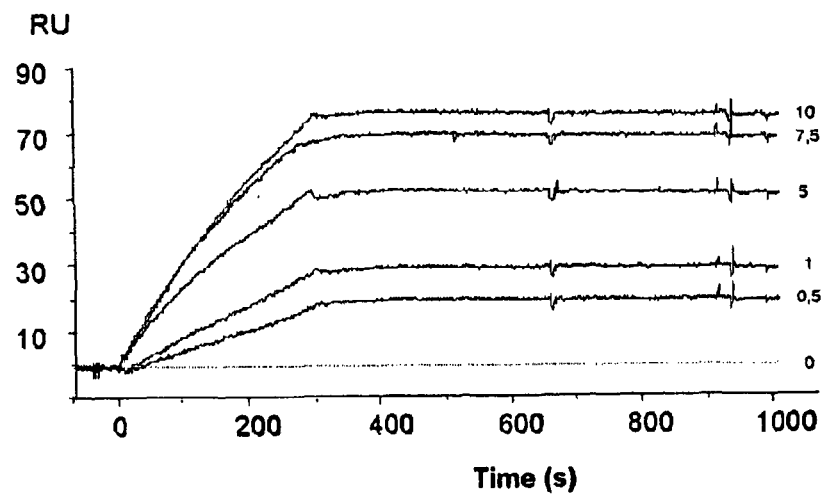
Figure 2:
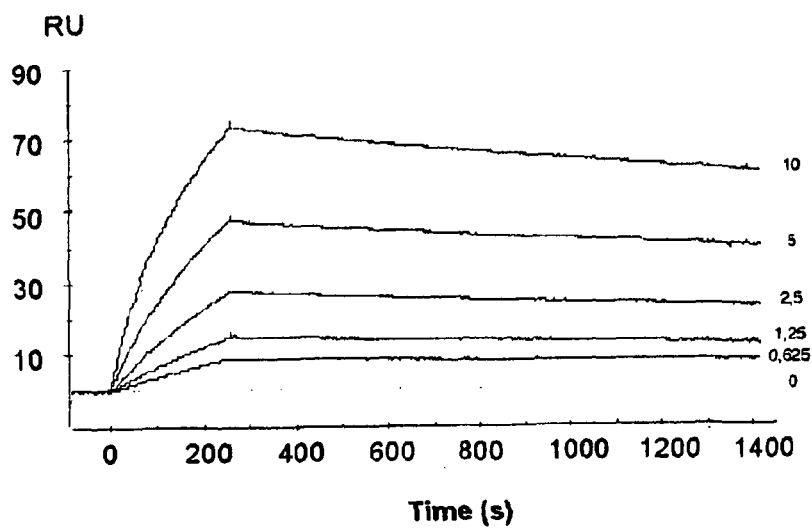

The affinities of the antibody for various recombinant proteins bearing the AviTag at the NH2 or COOH end were measured by surface plasmon resonance (BIACore AB, Uppsala, Sweden). The antibody AvT-6A8 was covalently coupled to the carboxymethyl dextran surface of a BIACore CM5 chip following the manufacturer's instructions. The amount of bound antibody was adjusted to give 1000 RU (resonance units). Binding of the different analytes to the bound antibody was measured at 25° C. with a flow rate of 40 µl/min. Sensorgrams were analysed with the BIA Evaluation Software 3.2. The best fit of experimental curves was obtained using a simple model of interaction (Langmuir) with a stoichiometry of 1:1. On FIG. 2A are shown the sensorgrams obtained with various concentrations of AviTag-4-1 BBL (tag on Nter). As indicated, calculated kinetic constants were $k_{on}=1.89\ 10^4\ M^{-1}s^{-1}$ and $k_{off}=1.94\ 10^{-5}\ s^{-1}$, which give a global affinity of AvT-6A8 for AviTag-4-1BBL of $Kd=1.03\ 10^{-9}$ M. On FIG. 2B, similar sensorgrams represent the binding of an HLA-A0201/Melan-A peptide A27L/β2 microglobulin complex (Vignard et al, J. Immunol., 2005) in which the heavy chain of HLA-A0201 includes the AviTag at the COOH end (called monomer Avitag-A2/Melan-A for short). The measured affinity of the antibody AvT-6A8 for this complex was $6.11\ 10^{-9}$ M (Kd). In conclusion, these results confirm the ELISA results and demonstrate that the monoclonal antibody AvT-6A8 has a strong affinity for the Avitag placed in NH2 and in COOH position, possibly with a slight preference for the AviTag placed at the NH2 end.

TABLE I reactivity of the different hybridomas selected after screening (A) and after subcloning (B).

A

| Hybridomas | First screen | | Second screen following amplification | | | |
|---|---|---|---|---|---|---|
| | SMCC-OVA | BDB-OVA | SMCC-OVA | BDB-OVA | OVA | AVITAG-4-1BBL |
| 2B6 | 1659 | 54 | 2664/2086/1795 | 0/0/52 | 0/0/0 | 42/0 |
| 11H7 | 1937 | 1397 | 1517/220 | 1007/188 | 0/7 | 290/210 |
| 6B3 | 735 | 599 | 502/104/179 | 390/106/181 | 77/86/0 | 0/0 |
| 6C4 | 457 | 411 | 274/86/44 | 168/52/78 | 14/09/00 | 0/0 |
| 6G5 | 642 | 422 | 699/104/179 | 470/141/136 | 78/135/0 | 0/0 |
| 6A8 | 1508 | 1391 | 2303/1870/2436 | 2036/1988/2901 | 13/57 | 1278/1975 |
| 8H5 | 724 | 611 | 326/711/661 | 468/777/791 | 1063/751/324 | 0/359 |
| 8C12 | 628 | 307 | 481/169/280 | 392/0/334 | 302/255 | 0/0 |
| 10F11 | 553 | 116 | 871/613 | 168/78 | 31/18 | 34/0 |
| 11G11 | 1334 | 664 | 805/1003 | 435/1079 | 6/751 | 877/315 |
| 11F4 | 766 | 109 | 273/460 | 256/134 | 90/52 | 17/111 |

B

| Sub-clones | Reactivity following cloning and sub-cloning | | | |
|---|---|---|---|---|
| | SMCC-OVA | BDB-OVA | OVA | AVITAG-4-1BBL |
| 6A8F4C10 | 1769/1772 | 1850/1872 | 30/4 | 1459/1491 |
| 6A8F4F12 | 1695/1745 | 1813/1777 | 19/0 | 1520/1469 |

Results are expressed as OD at 492 nm.
Values separated by a slash represent different measurements of the same supernatant.

Example 2
Affinity Chromatography Using the AvT-6A8 Monoclonal Antibody

We evaluated the efficiency of affinity chromatography with the antibody AvT-6A8 to purify recombinant proteins comprising the AviTag. To this end, we covalently coupled 20 mg of purified AvT-6A8 on a HiTrap NHS-activated column (Amersham Biosciences) according to the manufacturer's instructions. In brief, the antibody was loaded on the column in 5 ml of NaHCO$_3$ 0.2M NaCl 0.5M buffer and incubated for 30 minutes at 25° C. and then an elution was performed to evaluate the yield of coupling. This yield was evaluated at 98.7%. Free NHS groups on the column were inactivated by ethanolamine.

Figure 3:
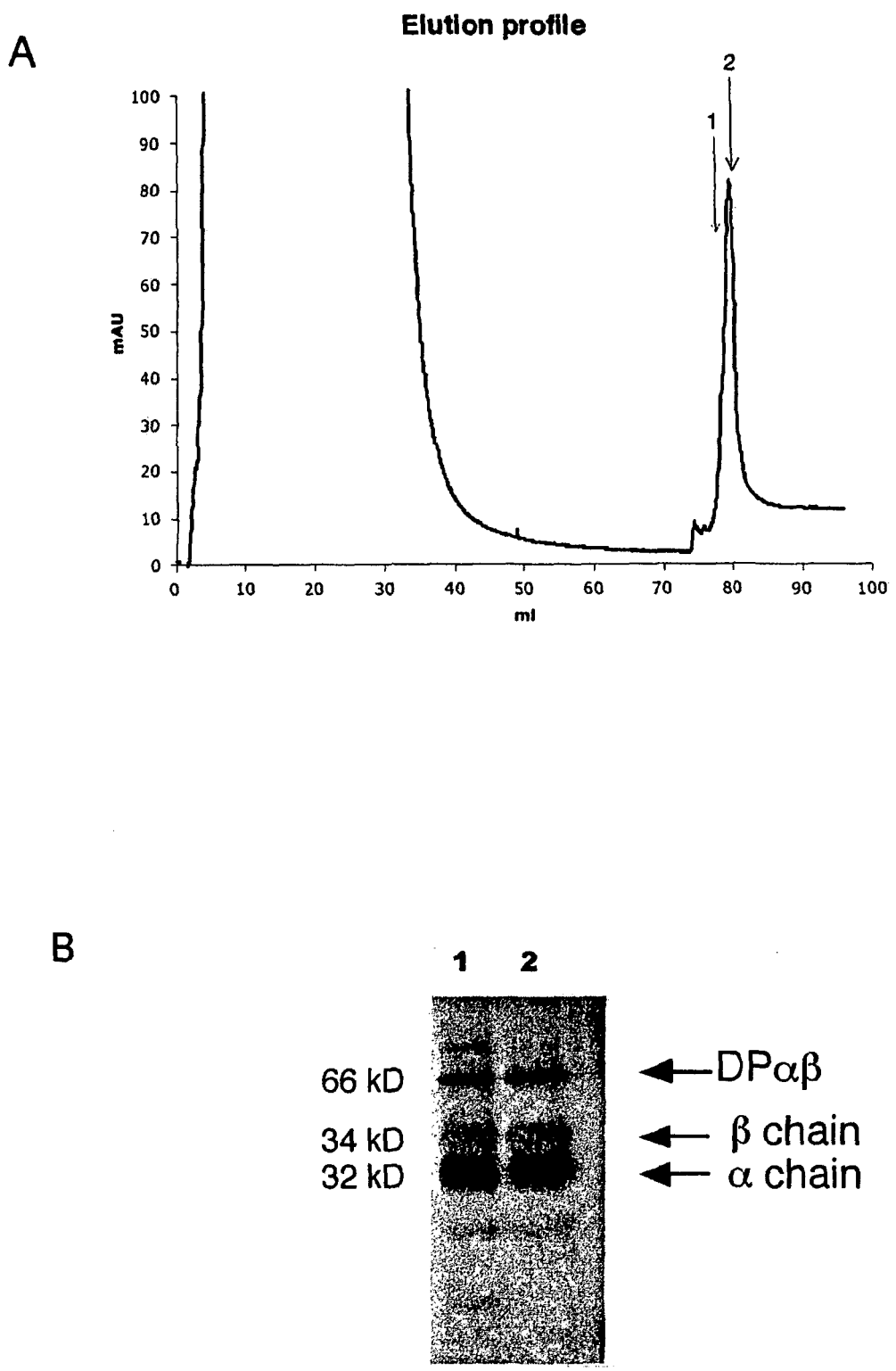

In parallel, we produced in S2 *Drosophila* cells a DPA0103/DPB0401 class II HLA complex in which the DPB chain bears the AviTag peptide at the COOH end as previously described (Yang et al, J. Clin. Immunol., 2005). We have loaded 25 ml of a 5 day supernatant from transfected and induced S2 cells onto the AvT-6A8 affinity column in citrate buffer pH=6.2. After washes, elution was performed by decreasing the pH to 3 and increasing the ionic strength to 0.5M NaCl. The elution profile is shown on FIG. 3A. Analysis of the peak of elution by SDS PAGE confirmed the purity of the eluted DPA0103/DPB0401 complex (FIG. 3B). The flow-through contained no complex.

Thus, the inventors have demonstrated that a polypeptide tagged in its NH2 terminus or its COOH terminus with SEQ ID No. 1 can be efficiently purified by the method of the invention.

Example 3
Cell Sorting Using Magnetic Beads Coated with the AvT-6A8 Monoclonal Antibody In this example, an HLA-A2-AviTag/MelanApeptide/β2 microglobulin complex taken as an example of an MHC/peptide complex bearing the AviTag at the COOH end of the heavy chain. This HLA-A2/Melan-A complex is the same as the one routinely biotinylated and either tetramerized with streptavidin to stain Melan-A specific T lymphocytes or coated on streptavidin magnetic beads to sort Melan-A specific T lymphocytes (Vignard et al, J. Immunol., 2005). Magnetic beads (M450 epoxy Dynabeads®) covalently coupled to the monoclonal antibody AvT-6A8 and coated with MHC/peptide complexes can be used to perform immuno-magnetic sorting of T lymphocytes specific for the selected MHC/peptide complexes.

Figure 4:
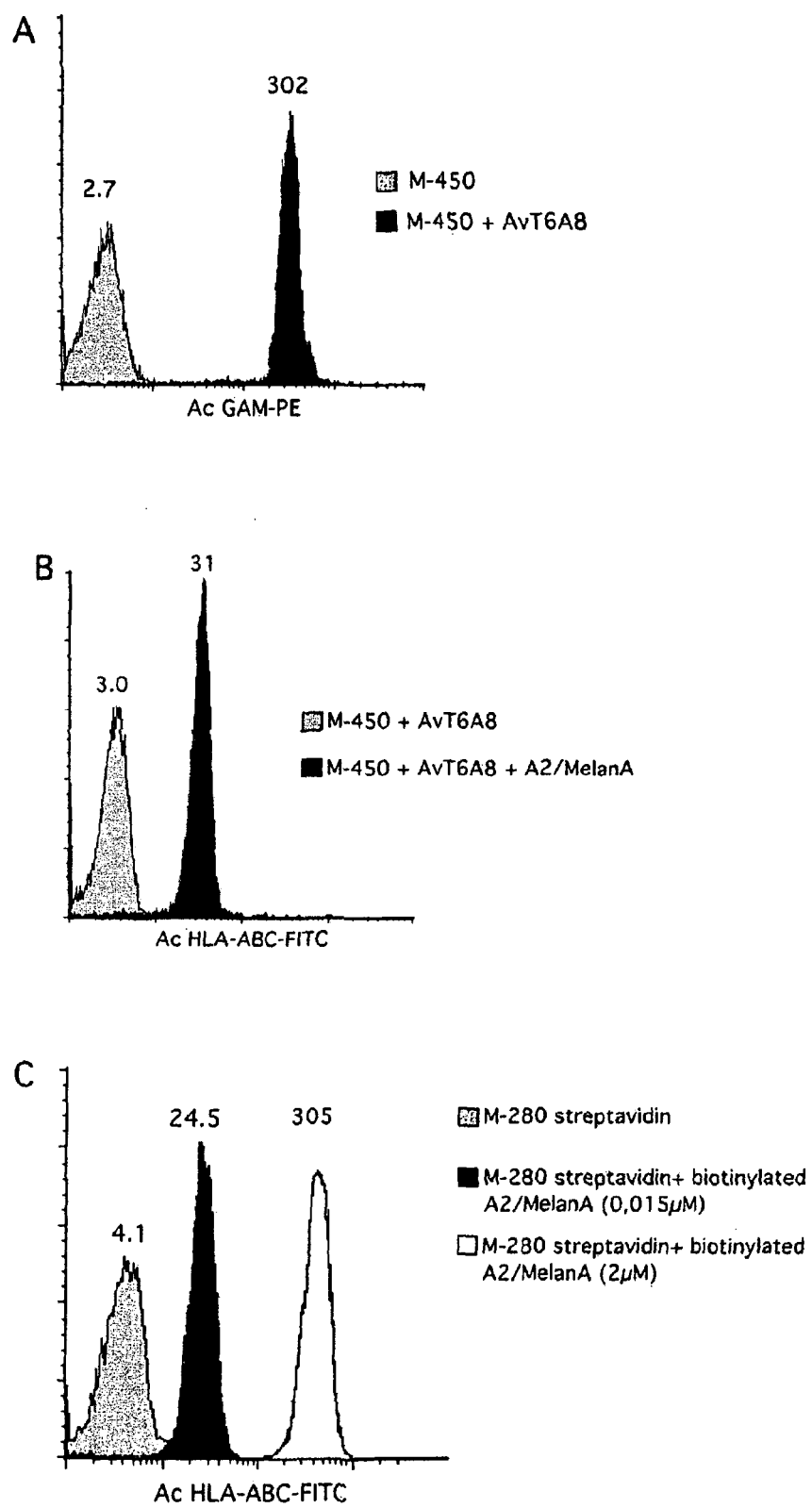

Immuno-Magnetic Sorting of T Lymphocytes Specific for a HLA-A0201/Melan-A Peptide Complex On FIG. 4A is shown the result of the covalent coupling of 10 μg of AvT-6A8 to $10^7$ M450 epoxy magnetic beads for 1 hour at room temperature in borate buffer pH8.2. After washes, with PBS-BSA 0.1%, a sample of the beads were labelled for 1 hour at 4° C. with a PE-conjugated anti-mouse Ig antibody (GAM-PE, Becton Dickinson) and analyzed by flow cytometry. The labelling histogram showed that all beads were highly fluorescent (mean fluorescence intensity (MFI) of 300) indicating that they were very efficiently coupled to high amounts of AvT-6A8. These beads coupled to AvT-6A8 were then incubated with 1 μg of monomer Avitag-A2/Melan-A in PBS-0.1% BSA for 1 hour at 4° C. Then, a sample of those beads were labelled for 1 hour at 4° C. with an FITC-conjugated anti-HLA ABC antibody (Becton Dickinson) and analyzed by flow cytometry. As shown on FIG. 4B, a significant staining of the beads is observed confirming that the monomer Avitag-A2/Melan-A did bind to the beads. The relatively low fluorescence displayed by the saturated beads suggested that only a fraction of the AvT-6A8 was accessible to the monomer Avitag-A2/Melan-A probably as a result of random coupling of the antibody to the beads and steric hindrance. On panel C of FIG. 4 is shown the labelling of M280 streptavidin beads (Dynal) coated with different concentrations of biotinylated Avitag-A2/Melan-A with an FITC-conjugated anti-HLA ABC antibody. These M280 beads have a much higher capacity of binding of biotinylated Avitag-A2/Melan-A monomers than AvT-6A8 coated M450 beads: The mean fluorescence obtained with saturating amounts of monomers (2 μg) is 300 as compared to the MFI of 31 obtained with saturated AvT-6A8-beads. Therefore, for functional comparison of the two types of beads (see the apoptosis induction experiments), we prepared M280 beads with similar amounts of monomer (MFI of 24.5) than the saturated AvT-6A8-beads (MFI of 31) by lowering the concentration of biotinylated Avitag-A2/Melan-A monomers (0.015 μg) on Streptavidin M280 beads (FIG. 4C).

AvT-6A8-M450 beads coated with Avitag-A2/Melan-A monomers were then tested for their efficiency to sort T lymphocytes specific for this complex from polyclonal lymphocyte populations. As stated above, since these beads presented much less monomers at their surface than streptavidin M280 beads, it could not be anticipated whether the number of HLA complexes on each bead would be sufficient to efficiently bind and sort specific T lymphocytes.

Figure 5:
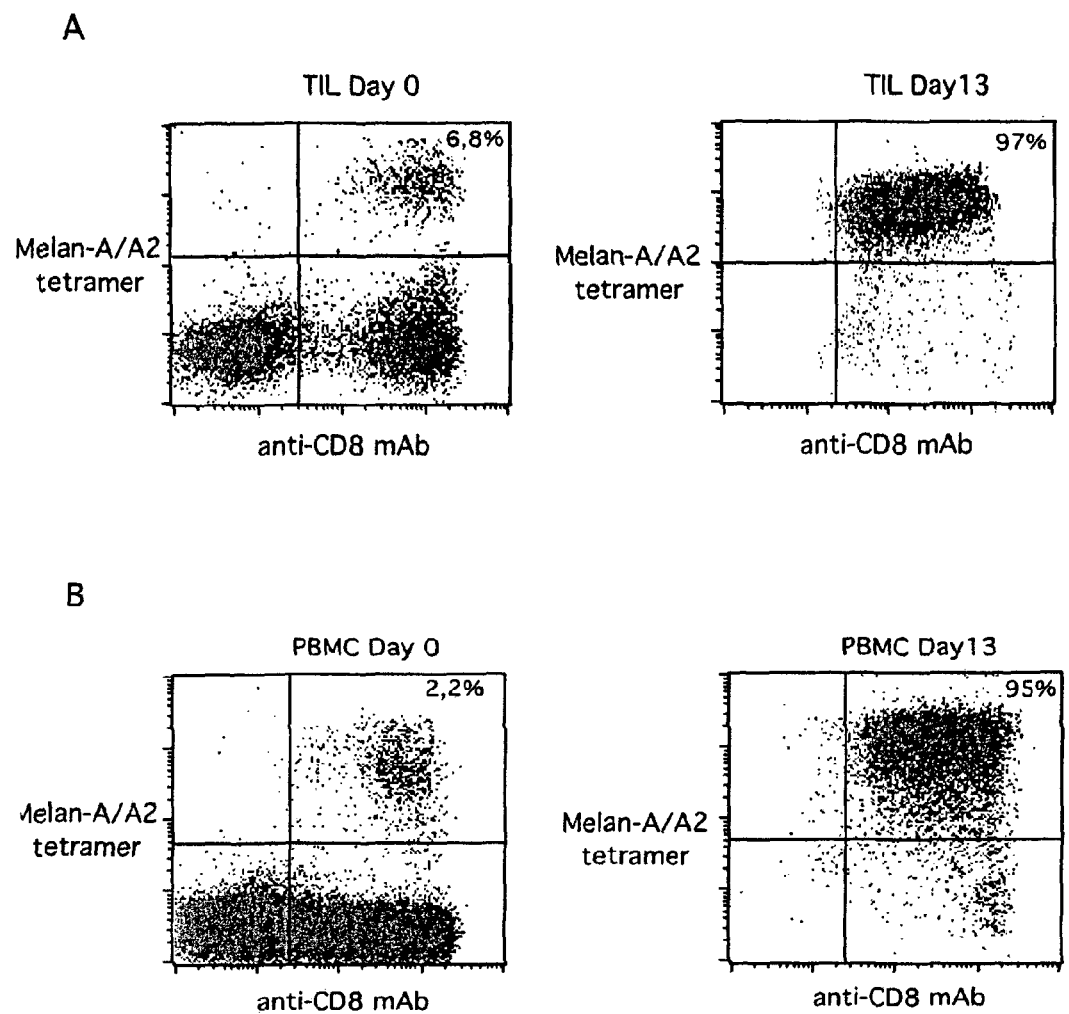

The first experiment consisted in sorting MelanA/A2 specific T lymphocytes from a polyclonal population of lymphocytes infiltrating a melanoma tumor (tumor infiltrating lymphocytes, TIL). The Melan-A/A2 specific lymphocytes represented 6.8% of the starting TIL population as measured by staining with a PE-conjugated HLA-A2/Melan-A tetramer (FIG. 5A). The TIL population ($4.10^6$ cells) was incubated for 4 hours at 4° C. with $5.10^6$ Avitag-A2/Melan-A coated beads in 100 μl of PBS 0.1% BSA on a rotating shaker. The lymphocytes that bound the beads were recovered with a magnet, washed several times and amplified for 13 days in vitro by non specific restimulation with irradiated feeder cells (Peripheral Blood Mononuclear Cells (PBMC) and secured EBV transformed B cell-lines), IL-2 and PHA-L as previously described (Labarrière et al, Int. J. Cancer, 2002). Following this 13 day expansion phase, $15.10^7$ lymphocytes were recovered and analyzed by staining with an HLA-A2/Melan-A tetramer (FIG. 5A, right panel). As shown, the population is almost pure (97%) in T lymphocytes specific for the selecting HLA-A/Melan-A complex.

A second sorting experiment was performed in the same conditions starting with PBMC from a melanoma patient that contained 2.2% Melan-A specific T cells as indicated by tetramer staining (FIG. 5B, left panel). Following the sort and the in vitro amplification, we obtained $2.10^7$ lymphocytes that were 95% pure in Melan-A/A2 specific T lymphocytes (FIG. 5B, right panel). The absolute numbers of specific lymphocytes recovered and the yield of the whole procedure in the two experiments are summarized in Table II. These results demonstrate that AvT-6A8 coupled M450 beads coated with Melan-A/A2 monomers can very efficiently sort specific T cells representing a few percent of the whole lymphocyte population and are thus as efficient as the previously described M280 streptavidine beads (Bodinier et al, Nat. Med., 2000).

TABLE II

Absolute numbers of specific lymphocytes recovered and yield of the cell sorting procedure

| | | patient 1 (TIL) | patient 2 (PBL) |
|---|---|---|---|
| Starting populations | Total cell number | $4\,10^5$ | $2\,10^6$ |
| | % of specific cells | 6.8 | 2.23 |
| | Number of specific cells | $2.710^5$ | $4.510^4$ |
| D13 following sort and amplification | Number of amplified cells | $1.510^8$ | $210^7$ |
| | % specific cells | 97 | 95 |
| | Number of specific cells | $1.4510^8$ | $1.910^7$ |
| | Amplification factor | X537 | X422 |

Apoptosis Induction of T Lymphocytes by HLA/Peptide Coated Beads

Figure 6:
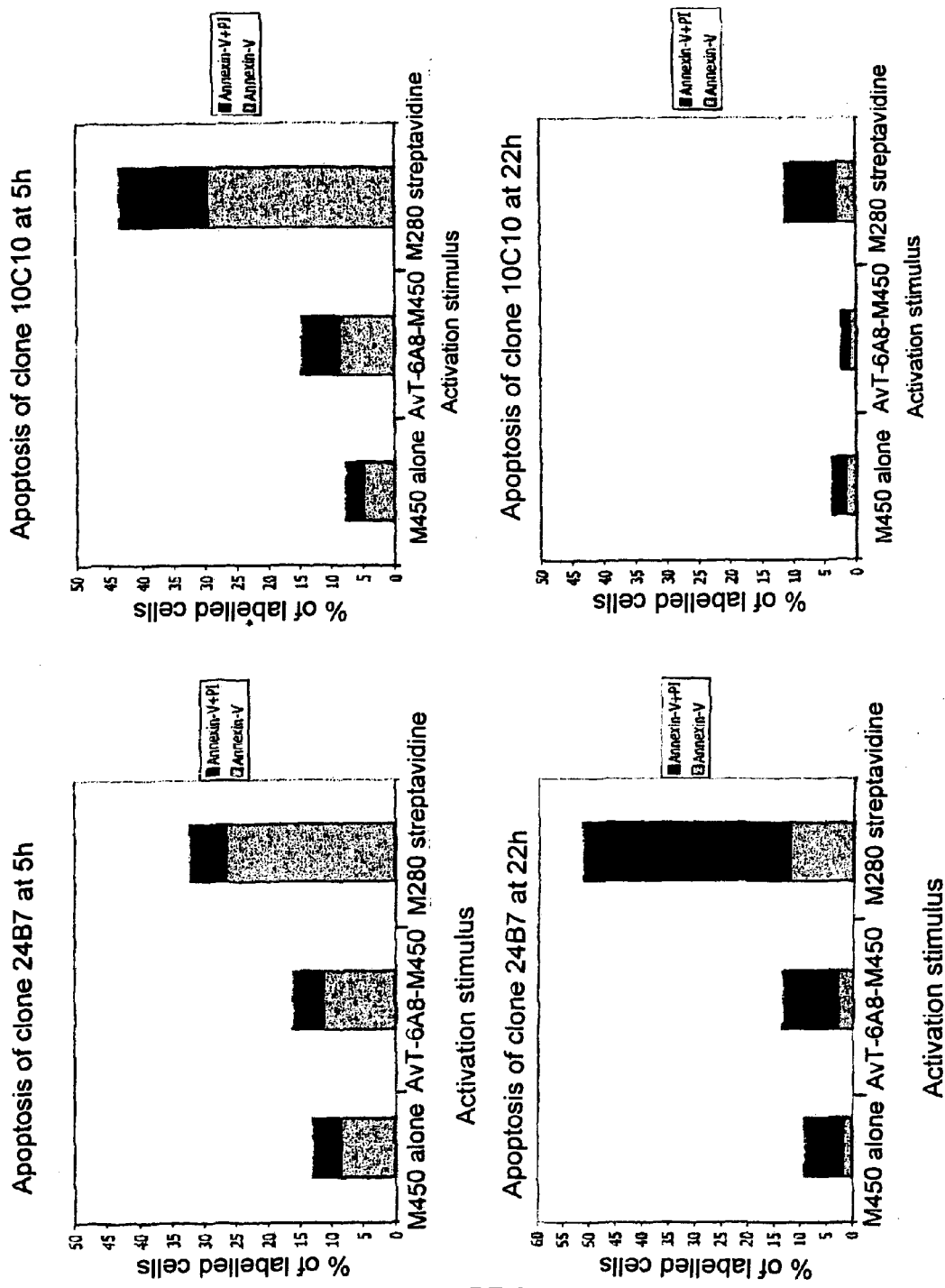

The ability of AvT-6A8-M450 beads and streptavidin M280 beads coated was compared with the same amount of A2/Melan-A monomers (as discussed above and FIG. 4C) to induce apoptosis of two previously described T cell clones specific for Melan-A/A2 (Vignard et al, J. Immunol., 2005). The T cell clones 24B7 and 10C10 were incubated at 37° C. with either M450 beads alone, Melan-A/A2-AvT-6A8-M450 beads or Melan-A/A2-streptavidine M280 beads in RPMI 10% human serum ($2.10^5$ cells/well) for 5 h or 22 h at a cell/bead ratio of 1:1. After incubation, cells were doublestained with annexinV-FITC, an early marker of apoptosis and propidium iodide (PI), a late marker of apoptosis. The results are shown on FIG. 6. For clone 24B7, a 5 hour incubation with Melan-A/A2-streptavidine M280 beads triggered apoptosis in 32% of the cells. Most of the apoptotic cells were in an early phase since they were stained with annexin V but not with PI. After 22 hours with the same beads, we detected 52% of apoptotic cells and most of them were double stained indicating that the cells progressed to a late phase of the apoptotic program. In marked contrast, incubation with Melan-A/A2-AvT-6A8-M450 beads induced only a very small increase in apoptosis as compared to unstimulated cells (16% vs 13%, respectively). For clone 10C10, very similar observations could be made although the kinetics of apoptosis were much faster than with 24B7. In fact, most of the apoptosis occurred before 22 hours so that at 22 hours, most apoptotic cells had turned into undetectable cell debris. Nevertheless, after 5 hours of incubation, we could evidence a strong induction of apoptosis by Melan-A/A2-streptavidine M280 beads (44%) whereas Melan-A/A2-AvT-6A8-M450 beads induced only a small increase in apoptotic cells as compared to unstimulated cells (15% vs 8%, respectively).

These results provide solid evidence that Melan-A/A2-streptavidine M280 beads induce a strong apoptotic signal by crosslinking TCRs whereas Melan-A/A2-AvT-6A8-M450 beads do not.

In conclusion, M450 magnetic beads covalently coupled to the monoclonal antibody AvT-6A8 and coated with HLA/peptide complexes represent the ideal tool for sorting specific T lymphocytes since they can bind to the cells without inducing activation or apoptosis. The inventors thus demonstrate that this novel procedure for immunomagnetic T lymphocyte sorting is at least, as efficient as the previously described sorting procedure (Bodinier et al, Nature Medicine, 2000 and patent WO 0118053) using streptavidin beads coated with biotinylated MHC/peptide complexes with two major and inventive advantages:

The Avt-6A8 beads coated with MHC/complexes induce no apoptosis of the specific T lymphocytes to which they bind, contrary to streptavidin beads coated with biotinylated MHC/peptide complexes;

AvT-6A8 beads can be easily produced in GMP grade (whereas solid supports using native or modified streptavidin are not available in GMP grade) and thus, provided that MHC/peptide complexes are also produced in GMP conditions, the whole sorting procedure can be adapted to a clinical setting.

REFERENCES

All the references cited are incorporated herein by reference.

Altman J D, Moss P A, Goulder P J, Barouch D H, McHeyzer-Williams M G, Bell J I, McMichael A J, Davis M M, Phenotypic analysis of antigen-specific T lymphocytes. Science. 1996 Oct. 4; 274(5284):94-6.

Barbas C F, Bain J D, Hoekstra D M, Lerner R A. (1992), Semisynthetic combinatorial antibody libraries: a chemical solution to the diversity problem. PNAS USA, 89, 4457-4461.

Bodinier M, Peyrat M A, Tournay C, Davodeau F, Romagne F, Bonneville M, Lang F. Efficient detection and immunomagnetic sorting of specific T cells using multimers of MHC class I and peptide with reduced CD8 binding. Nat. Med. 2000 June; 6(6):707-10. Harlow E. et al., Antibodies: A Laboratory Manual, Cold Spring Harbor Laboratory, New York, (1988).

Cebecauer M., Guillaume P, Hozak P, Mark S, Everett H, Schneider P, Luescher I F. Soluble MHC-peptide complexes induce rapid death of CDS+ CTL. J Immunol. 2005 Jun. 1; 174(11):6809-19.

Guillaume P, Baumgaertner P, Angelov G S, Speiser D, Luescher I F. Fluorescence-activated cell sorting and cloning of bona fide CD8+ CTL with reversible MHC-peptide and antibody Fab' conjugates. J Immunol. 2006 Sep. 15; 177 (6):3903-12.

Harlow E. et al., Antibodies: A Laboratory Manual, Cold Spring Harbor Laboratory, New York, (1988).

Kohler and Milstein (1975) Continuous cultures of fused cells secreting antibody of predefined specificity. Nature; 256, 495-7.

Luxembourg A. T. et al, Nature Biotechnology, vol. 16, March 1998, 281-285 Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

Rabu C, Quèmèner A, Jacques Y, Echasserieau K, Vusio F, Lang F. Production of recombinant human trimeric CD137L (4-1BBL). Cross-linking is essential to its T cell co-stimulation activity. J Biol Chem. 2005 Dec. 16; 280 (50):41472-81. Epub 2005 Oct. 4.

Riechmann L, Clark M, Waldmann H, Winter G Reshaping human antibodies for therapy. Nature. 1988 Mar. 24; 332 (6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Schatz P J. Use of peptide libraries to map the substrate specificity of a peptide-modifying enzyme: a 13 residue consensus peptide specifies biotinylation in *Escherichia coli*. Biotechnology (NY). 1993 October; 11(10):1138-43.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Vignard V, Lernercier B, Lim A, Pandolfino M C, Guilloux Y, Khammari A, Rabu C, Echasserieau K, Lang F, Gougeon M L, Dreno B, Jotereau F, Labarriere N. Adoptive transfer of tumor-reactive Melan-A-specific CTL clones in melanoma patients is followed by increased frequencies of additional Melan-A-specific T cells. J Immunol. 2005 Oct. 1; 175(7):4797-805.

Waterhouse P, Griffiths A D, Johnson K S, Winter G. Combinatorial infection and in vivo recombination: a strategy for making large phage antibody repertoires. Nucleic Acids Research. 1993, 21, 2265-2266.

Yang J, Huston L, Berger D, Danke N A, Liu A W, Disis M L, Kwok W W. Expression of HLA-DP0401 molecules for identification of DP0401 restricted antigen specific T cells. J Clin Immunol. 2005, 25(5), 428-436.

The invention claimed is:

1. An isolated antibody or a fragment thereof obtainable by the hybridoma deposited at the COLLECTION NATIONALE DE CULTURES DE MICROORGANISMES under the number CNCM 1-3767 which recognizes the sequence MSGLNDIFEAQKIEWHE (SEQ ID No. 1), wherein said antibody or said fragment thereof recognizes polypeptides containing SEQ ID No. 1 at their NH2 terminus and polypeptides containing SEQ ID No. 1 at their COOH terminus.

2. An isolated antibody or fragment thereof according to claim 1 wherein said antibody or fragment thereof displays the same antigen combining sites as the antibody obtainable by the hybridoma deposited at the CNCM under the number CNCM I-3767.

3. A hybridoma deposited at the COLLECTION NATIONALE DE CULTURES DE MICROORGANISMES (CNCM) under the number CNCM I-3767.

4. A solid support whereupon an antibody or a fragment thereof according to claim 1 is immobilized.

5. A solid support according to claim 4 wherein said solid support is a magnetic bead.

* * * * *

UNITED STATES PATENT AND TRADEMARK OFFICE
CERTIFICATE OF CORRECTION

Page 1 of 1

PATENT NO.       : 8,431,394 B2
APPLICATION NO.  : 12/668119
DATED            : April 30, 2013
INVENTOR(S)      : Lang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 431 days.

Signed and Sealed this
Fourth Day of November, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Tag

<400> SEQUENCE: 1

Met Ser Gly Leu Asn Asp Ile Phe Glu Ala Gln Lys Ile Glu Trp His
1               5                   10                  15

Glu

<210> SEQ ID NO 2
<211> LENGTH: 19
<212> TYPE: PRT
<213> ORGANISM: Artificial Sequence
<220> FEATURE:
<223> OTHER INFORMATION: Tag

<400> SEQUENCE: 2

Cys Met Ser Gly Leu Asn Asp Ile Phe Glu Ala Gln Lys Ile Glu Trp
1               5                   10                  15

His Glu Tyr
```